US008900112B2

(12) United States Patent
Holmes et al.

(10) Patent No.: US 8,900,112 B2
(45) Date of Patent: Dec. 2, 2014

(54) METHOD FOR OPTIMIZING SPIN TIME IN A CENTRIFUGE APPARATUS FOR BIOLOGIC FLUID

(75) Inventors: Brian M. Holmes, Evergreen, CO (US); Briden Ray Stanton, Highlands Ranch, CO (US); Geert Van Waeg, Brussels (BE); Robert Langley, Westminster, CO (US); Mary Langley, legal representative, Westminster, CO (US)

(73) Assignee: Terumo BCT, Inc., Lakewood, CO (US)

(*) Notice: Subject to any disclaimer, the term of this patent is extended or adjusted under 35 U.S.C. 154(b) by 789 days.

(21) Appl. No.: 13/176,466

(22) Filed: Jul. 5, 2011

(65) Prior Publication Data

US 2012/0015794 A1 Jan. 19, 2012

Related U.S. Application Data

(60) Provisional application No. 61/364,495, filed on Jul. 15, 2010.

(51) Int. Cl.
| | | |
|---|---|---|
| *B01D 21/26* | (2006.01) | |
| *B04B 5/04* | (2006.01) | |
| *A61M 1/36* | (2006.01) | |
| *B04B 13/00* | (2006.01) | |

(52) U.S. Cl.
CPC ............ *A61M 1/3693* (2013.01); *B04B 5/0428* (2013.01); *B04B 2013/006* (2013.01); *A61M 1/3698* (2013.01)
USPC .................................. 494/37; 494/11; 494/45

(58) Field of Classification Search
CPC .... B01D 21/26; B04B 5/0428; B04B 5/0442; B04B 2013/006; A61M 1/3693; A61M 1/3698
USPC ............ 494/1–3, 10, 11, 37, 43, 45; 210/782, 210/787; 604/6.01–6.06
See application file for complete search history.

(56) References Cited

U.S. PATENT DOCUMENTS

| | | |
|---|---|---|
| 4,187,979 A | 2/1980 | Cullis et al. |
| 6,284,142 B1 | 9/2001 | Muller |
| 6,592,507 B2 | 7/2003 | Jorgensen et al. |
| 7,347,932 B2 | 3/2008 | Holmes et al. |
| 7,442,178 B2 | 10/2008 | Chammas |
| 2008/0220959 A1 | 9/2008 | Holmes et al. |
| 2008/0283471 A1 | 11/2008 | Nazzer |

FOREIGN PATENT DOCUMENTS

| | | |
|---|---|---|
| EP | 1627651 A2 | 2/2006 |
| EP | 1757318 B1 | 11/2010 |
| WO | 2006/071496 A2 | 7/2006 |
| WO | 2009/134521 A1 | 11/2009 |

OTHER PUBLICATIONS

PCT/US2011/042959, "International Search Report", mailed Oct. 27, 2011.

*Primary Examiner* — Timothy Cleveland
(74) *Attorney, Agent, or Firm* — John R. Merkling

(57) ABSTRACT

A method for controlling a centrifuge blood component separation system for separating components of a blood product, the separation system comprising a centrifuge and a separation bag and at least one transfer bag. The method comprises selecting a nominal hematocrit value such that an actual hematocrit value is expected to be less than said nominal hematocrit; centrifuging a separation bag containing a volume of composite liquid so as to cause the sedimentation of at least a first component and a second component; transferring some of the first component to a first transfer bag; detecting time of passage of a red blood cell interface at a pre-selected location in the separation bag; and adjusting a predicted processing time based on the time of passage of the red blood cell interface.

10 Claims, 5 Drawing Sheets

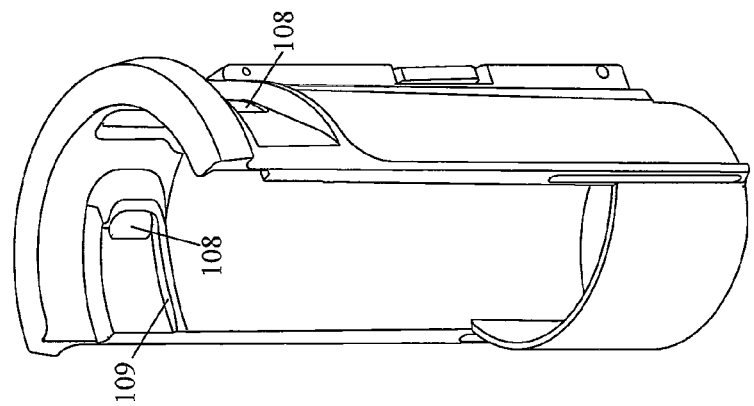
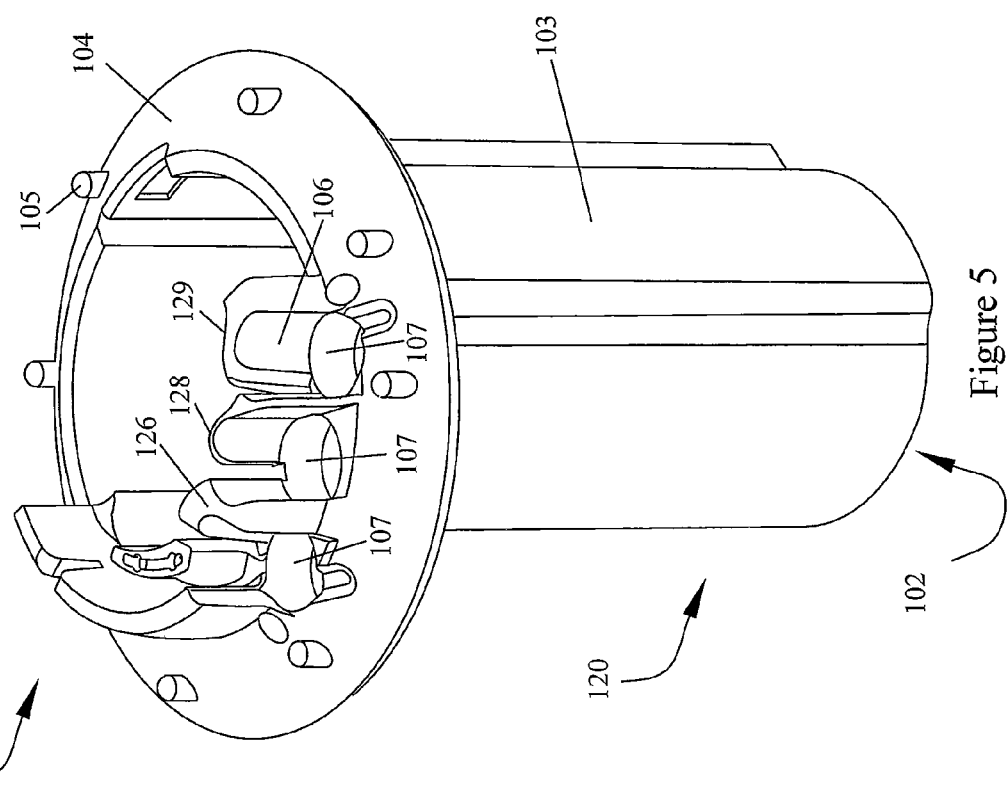

METHOD FOR OPTIMIZING SPIN TIME IN A CENTRIFUGE APPARATUS FOR BIOLOGIC FLUID

CROSS REFERENCE TO RELATED APPLICATIONS

This application claims the benefit of U.S. Provisional Application No. 61/364,495 filed Jul. 15, 2010.

FIELD OF THE INVENTION

The present invention concerns a method for separating a volume of composite biologic liquid or blood product into at least two components. The method optimizes the separation process for minimum separation time in a centrifuge apparatus for separating biologic fluids, such as blood.

Background

The apparatus and method of the invention are particularly appropriate for the separation of biological fluids comprising an aqueous component and one or more cellular components. For example, potential uses of the invention include extracting, from a volume of whole blood, a plasma component, a first cellular component including platelets, a second cellular component including mononuclear cells, and a third cellular component including red blood cells and granulocytes.

U.S. patent application Ser. No. 11/931,582 (filed Oct. 31, 2007) describes a method and an apparatus for separating a volume of whole blood into at least two components in accordance with various separation protocols. For example, one protocol provides for the separation of a volume of whole blood into a plasma component, a platelet component, and a red blood cell component. The apparatus comprises a centrifuge adapted to cooperate with various bag sets, in particular a bag set comprising an annular separation bag for whole blood, which is connected to a platelet component bag, a plasma component bag, and a red blood cell component bag. The centrifuge includes a rotor for spinning the separation bag and centrifuging the whole blood contained therein, the rotor having a turntable for supporting the separation bag and a central compartment for containing the component bags connected to the separation bag; a squeezing system for squeezing the separation bag and causing the transfer of the plasma component from the separation bag into the plasma component bag, of the red blood cell component into the red blood cell component bag, and of the platelet component into the platelet component bag. A centrifuge apparatus having a rotor with a central chamber receiving a rotor liner and transfer bag cradle is also disclosed in U.S. patent application Ser. No. 12/063,163.

SUMMARY OF THE INVENTION

One object of the invention is to provide a centrifuge apparatus for separating a composite liquid into at least a first component and a second component, comprising centrifuging a separation bag containing a volume of composite liquid so as to cause the sedimentation of at least a first component and a second component. The present invention seeks to reduce the duration centrifugation in a blood separation process by serially adjusting operating conditions in response to deviation of a condition or change in condition from an expected quality of that condition or time of change of that condition. In particular, it is recognized herein that the efficiency of a centrifugal blood separation apparatus may be improved by adjusting the processing time. In general, a predicted processing time for separating a unit of whole blood into component parts may be inaccurate because of uncertainties in certain parameters. For example, the actual volume of a blood unit may vary by as much as 10% from its nominal value. Sedimentation velocity also influences processing time and varies between different units of blood. Blood processors differ from other blood processors, even between blood processors of the same commercial model. Finally, the hematocrits of different units of blood also vary on the order of 10%. The hematocrit of a particular unit of blood may not be known precisely. If it is assumed that the hematocrit of the unit is high (to assure complete processing), the duration of processing will generally be longer than necessary, and the separation process overall will be less efficient. This inefficiency would be compounded over many units of blood processed on many different machines.

It is an object of the present invention, therefore, to improve the efficiency of a centrifugal blood processing apparatus by reducing processing time. In particular, the invention uses iterative methods to correct processing time. The method employs regression analysis to correct a predicted spin time by determining when a red blood cell interface arrives at or crosses a sensing location. The method may comprise setting an initial hematocrit estimate at a high value; placing a detector at a selected location in a blood processing apparatus; detecting the arrival of a blood component interface at the selected location; re-determining an expected processing duration from the arrival time of the interface; and continuing to separate blood. Preferably, a sensor for detecting the arrival of the interface is placed at a location near one half nominal spin time, that is, near a location where an RBC (red blood cell) interface would be expected after centrifugation for about half of the expected processing time. Detection of the RBC interface allows the apparatus to predict an adjusted processing time from the difference between the expected RBC interface arrival time and the actual RBC interface arrival time.

Other features and advantages of the invention will appear from the following description and accompanying drawings, which are to be considered exemplary only.

BRIEF DESCRIPTION OF THE DRAWINGS

FIG. 5 is a perspective view of a rotor liner for use in the rotor of FIG. 3.

FIG. 6 is a perspective view of a bag cradle for use in the rotor liner of FIG. 5.

DESCRIPTION OF THE EMBODIMENTS

For the sake of clarity, the invention will be described with respect to a specific use, namely the separation of whole blood into four components, namely a plasma component, a platelet component, a mononuclear cell component, and a red blood cell component. It should be understood however that this specific use is exemplary only. It should also be understood that the principles can be used for collecting at least two components.

Figure 1:
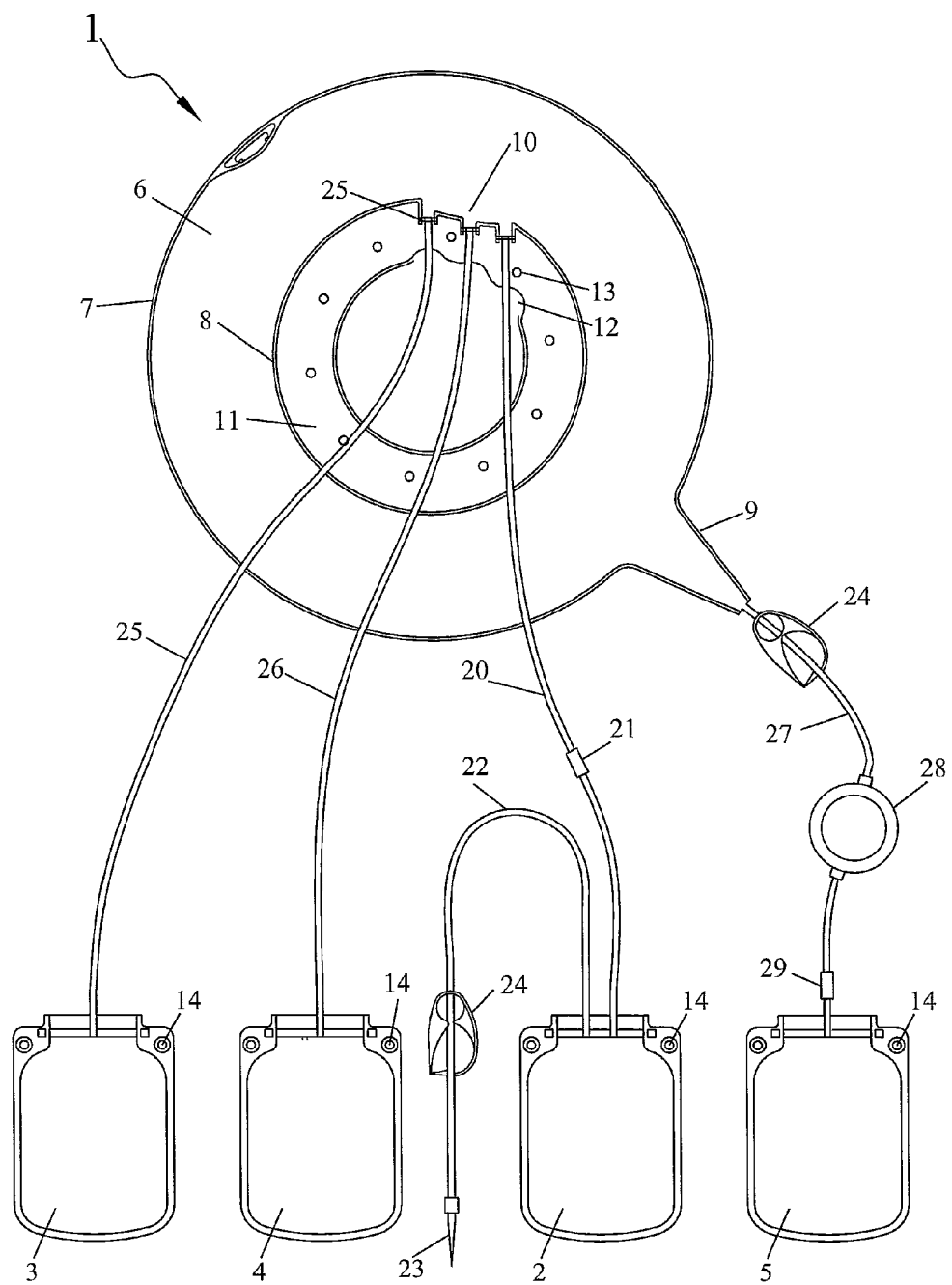
FIG. 1 is a schematic view of a set of bags designed for cooperating with a separation apparatus according to the invention.
Figure 2:
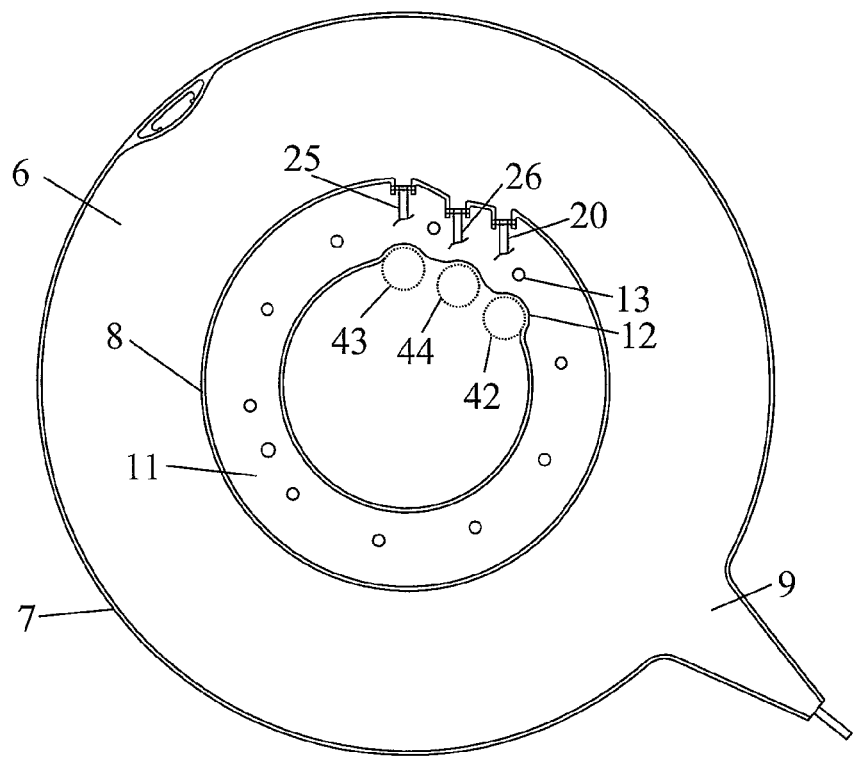
FIG. 2 is a top view of the separation bag of the set of bags of FIG. 1.
Figure 7:
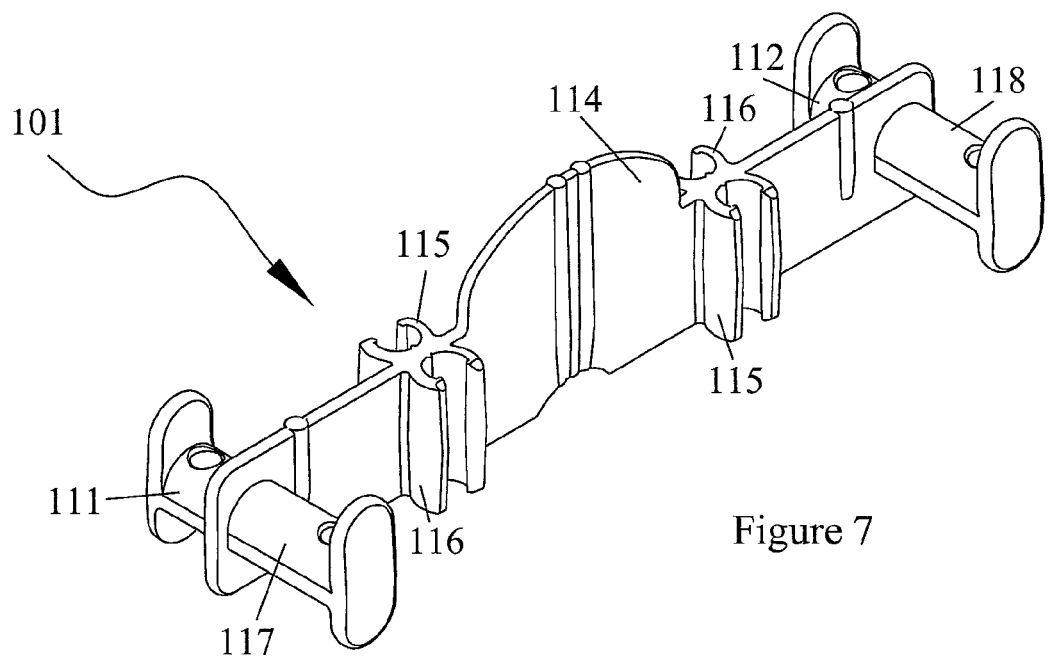
FIG. 7 is a perspective view of a bag-holder for use with the bag cradle of FIG. 6.

FIGS. 1 and 2 show an example of a set of bags adapted to the separation of whole blood into a plasma component (essentially comprising plasma), a platelet component (essentially comprising platelets), a mononuclear cell component (comprising monocytes, lymphocytes and some red blood cells) and a red blood cell component (essentially comprising red blood cells and granulocytes). This bag set comprises a flexible separation bag 1 and four flexible transfer bags 2, 3, 4, 5 connected thereto. The separation bag 1 comprises an annular separation chamber 6 having generally circular outer and inner edges 7, 8. The outer circular edge 7 and the inner circular edge 8 of separation chamber 6 are substantially concentric. Separation chamber 6 comprises a first, acute-angled, funnel-like extension 9 protruding outwardly from its outer edge 7 for helping drain a content of the separation chamber 6 into transfer bag 5. Separation chamber 6 also comprises a second, obtuse-angled, funnel-like extension 10 protruding from inner edge 8, towards the center of bag 1, for helping funnel separated components into first, second and third transfer bags 2, 3, 4.

Separation bag 1 further comprises a semi-flexible disk-shaped connecting element 11 that is connected to inner edge 8 of annular chamber 5. Disk-shaped connecting element 11 comprises three rounded recesses 12 on its inner edge facing second funnel-like extension 10, for partially surrounding three pinch valve members of a rotor of a centrifuge to be described later (diagrammatically shown in dotted line in FIG. 2). Disk-shaped connecting element 11 comprises a series of holes 13 for connecting separation bag 1 to the rotor of a centrifuge.

Transfer bag 2 has two purposes, and is successively used as a whole blood collection bag and as a mononuclear cell component bag. Transfer bag 2 is intended for initially receiving a volume of whole blood from a donor (usually about 450 ml) before the separation process, and the mononuclear cell component during the separation process. Transfer bag 2 is flat, substantially rectangular, and comprises two reinforced ears at its upper corners having holes 14 for hanging the bag. It is connected to separation bag 1 by transfer tube 20 having a first end connected to the upper edge of transfer bag 2 and a second end connected to the second funnel-like extension 10, close to inner circular edge 8. Transfer bag 2 contains a volume of anti-coagulant solution (typically about 63 ml of a solution of citrate phosphate dextrose for a blood donation of about 450 ml). A frangible connector 21 mounted on transfer tube 20 blocks a liquid flow through transfer tube 20 and prevents the anti-coagulant solution from flowing from transfer bag 2 into separation bag 1. The bag set further comprises a collection tube 22 that is connected at one end to the upper edge of transfer bag 2 and comprises, at the other end, a needle protected by a sheath 23. Collection tube 22 is fitted with a clamp 24.

Transfer bag 3 is intended for receiving a plasma component. Transfer bag 3 is flat, substantially rectangular, and comprises two reinforced ears at its upper corners having holes 14 for hanging the bag. It is connected by a transfer tube 25 to separation bag 1. Transfer tube 25 has a first end connected to the upper edge of transfer bag 3 and a second end connected to the second funnel-like extension 10, close to inner circular edge 8, opposite the second end of the first transfer tube 20 with respect to the tip of the second funnel-like extension 10.

Transfer bag 4 is intended for receiving a platelet component. It is flat, substantially rectangular, and comprises two reinforced ears at its upper corners having holes 14 for hanging the bag. It is connected by a transfer tube 26 to the separation bag 1. Transfer tube 26 has a first end connected to the upper edge of transfer bag 4 and a second end connected to the tip of the second funnel-like extension 10.

Transfer bag 5 is intended for receiving a red blood cell component. It is flat, substantially rectangular, and comprises two reinforced ears at its upper corners having holes 14 for hanging the bag. It is connected by a transfer tube 27 to separation bag 1. Transfer tube 27 has a first end connected to the upper edge of transfer bag 5 and a second end connected to the tip of the first funnel-like extension 9. It comprises two tube segments respectively connected to the inlet and the outlet of a leukoreduction filter 28. The tube segment connected to separation bag 1 is fitted with a clamp 24. The tube segment connected to transfer bag 5 is fitted with a frangible connector 29, which, when broken, allows a flow of liquid between separation bag 1 and transfer bag 5. The filter may be, for example, a filter of the type RC2D manufactured by Pall Corporation. Such a filter comprises a disk-shaped casing to which radial inlet and outlet ports are connected, in diametrical opposition. The casing, which is made of polycarbonate (GE LEXAN™ HF 1140), has an internal volume of about 33 ml. It is filled with a filtering medium composed of multiple layers of a non-woven web of polyester fibers (about two micron diameter). It is understood, however, that other filters by other manufacturers can also be used. Transfer bag 5 contains a volume of storage solution for red blood cells.

Figure 3:
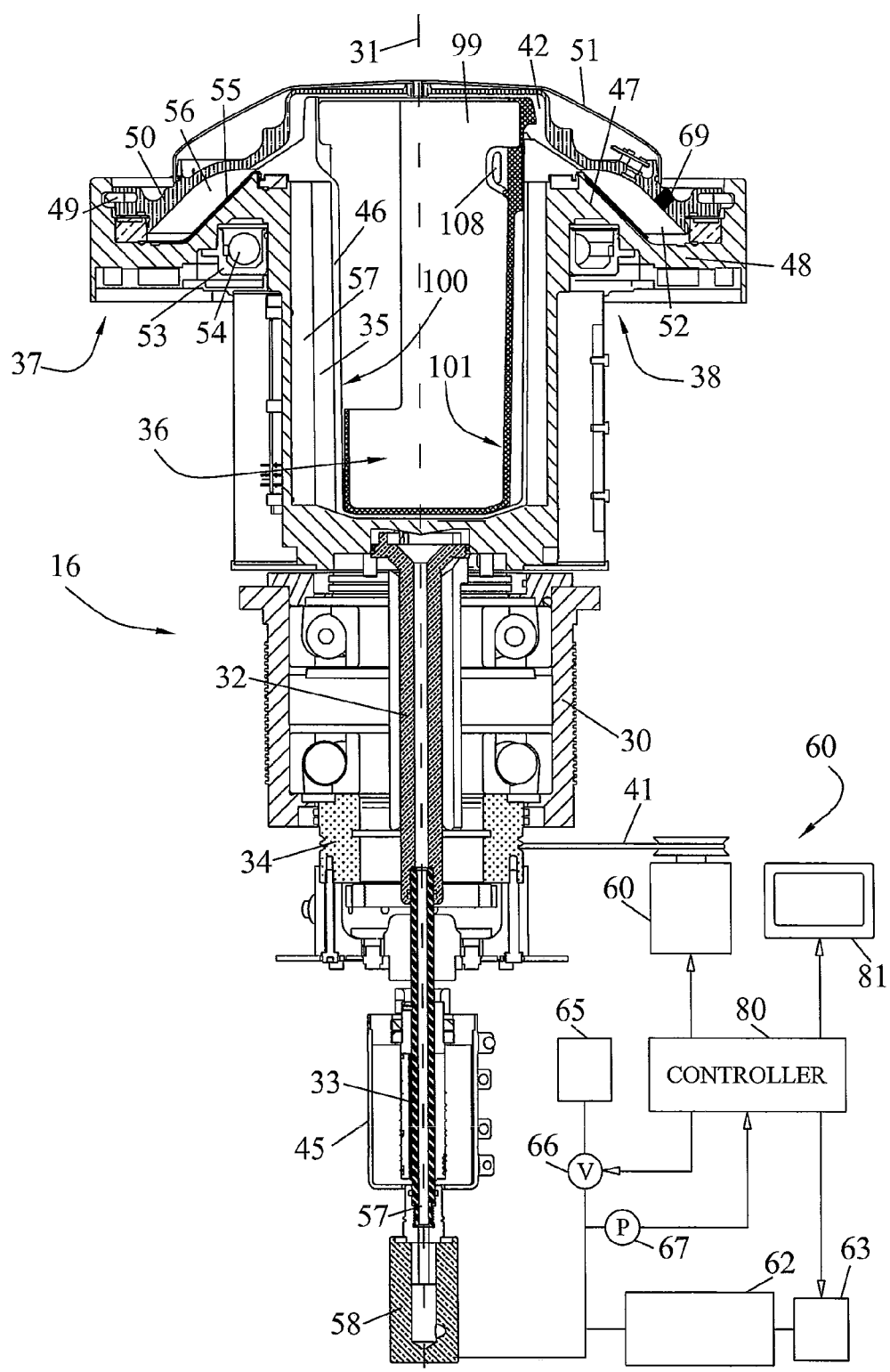
FIG. 3 is a schematic view, partly in cross-section, of a centrifugal separation apparatus, including a rotor.

Variants of the separation bag 1 may include a separation chamber 6 having an outer circular edge 7 and/or an inner circular edge 8 that are eccentric. Alternatively, a separation chamber 6 may comprise a radial wall extending from inner edge 8 to outer edge 7 so that chamber 6, instead of being annular, is C-shaped. A separation chamber 6 having any shape including an inner edge and an outer edge (the inner edge being closer to the axis of the rotor of a centrifuge than the outer edge, when the separation bag is mounted on the rotor of a centrifuge), for example the shape of a portion of annulus delimited by two lateral radial edge or a rectangular shape may also be used. In this variant, all the transfer bags may be connected to the inner edge of the separation bag. Also, the separation bag 1 can be shaped so as to fit either on a flat support surface or on a frustro-conical support surface of the rotor of a centrifuge. The bags and the tubes of the bag set shown in FIGS. 1, 2 and 3 are all made of flexible plastic material appropriate to contact blood and blood components.

Figure 4:
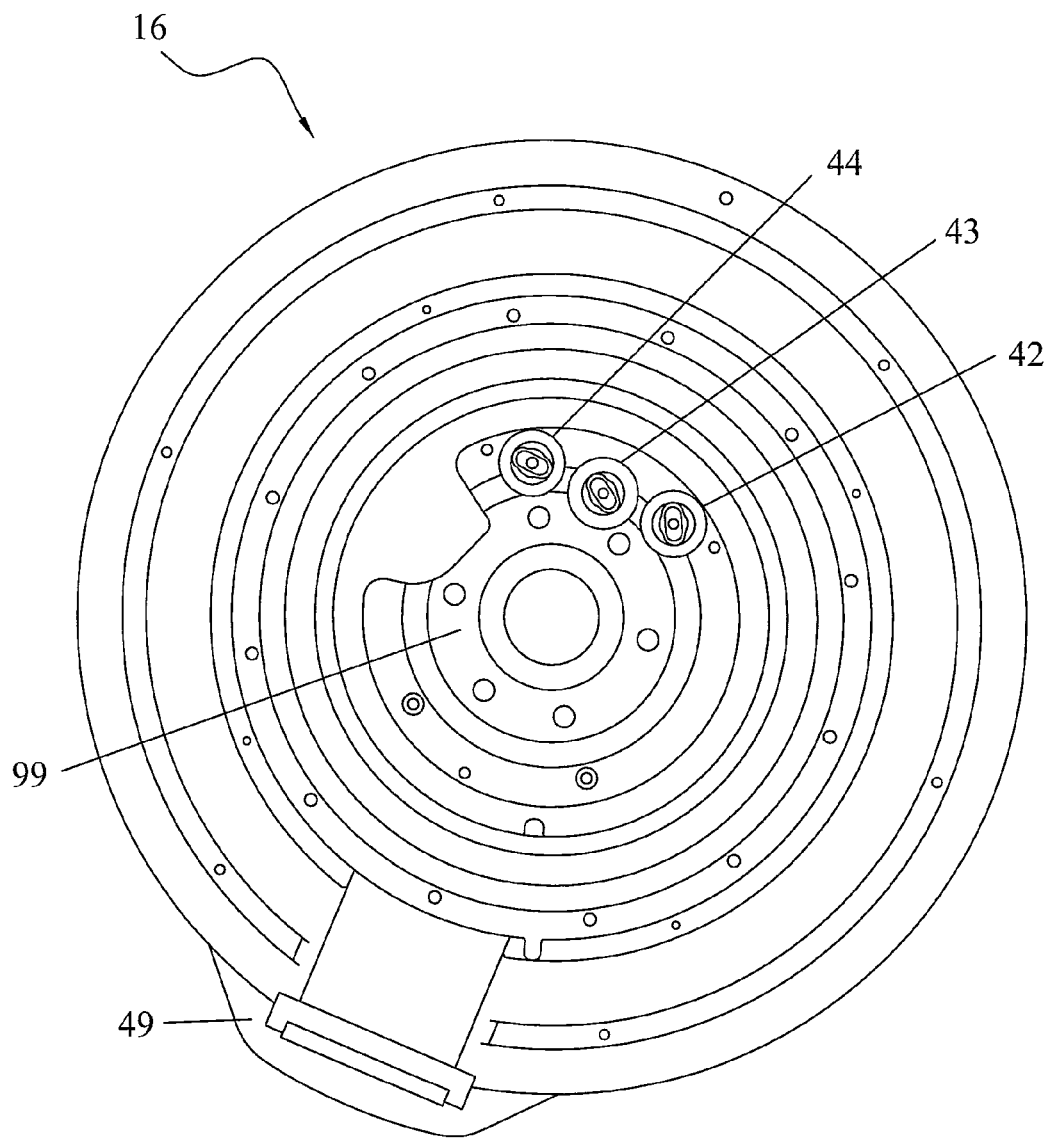
FIG. 4 is a top plan view of the rotor of FIG. 3.

FIGS. 4 and 5 show an embodiment of an apparatus for separating a volume of blood by centrifugation. The apparatus comprises a centrifuge adapted for receiving the set of separation bags shown in FIGS. 1, 2 and 3, and a component transferring means for causing the transfer of separated components into the transfer bags. The centrifuge comprises a rotor 16 that is supported by a bearing assembly 30 allowing the rotor 16 to rotate about a vertical central axis 31. The rotor 16 comprises a cylindrical rotor shaft comprising a first upper portion 32 and a second lower portion 33; the upper portion 32 of the shaft extends in part through the bearing assembly 30; a pulley 34 is connected to the lower end of the upper portion 32 of the shaft; a central compartment 35 for containing transfer bags, which is connected to the rotor shaft 32, 33 at the upper end thereof; a support member 36 fitting within the central compartment 34, for supporting at least one transfer bag in a determined position within the central compartment 35; a circular turntable 37 for supporting a separation bag, which is connected to the compartment 35 at the upper end thereof, the central axes of the rotor shaft 32, 33, the compartment 35 and the turntable 37 coinciding with the rotation axis 31; and a balancing assembly 38, which is secured to the turntable 37. The centrifuge further comprises a motor 40 coupled to the rotor 16 by a belt 41 engaged in a groove of the pulley 34 so as to rotate the rotor 16 about the central vertical axis 31.

The separation apparatus further comprises pinch valve members 42, 43, 44 that are mounted on the rotor 16 for selectively blocking or allowing a flow of liquid through a flexible plastic tube, and selectively sealing and cutting a plastic tube. Each pinch valve member 42, 43, 44 comprises an elongated cylindrical body and a head having a groove that is defined by a stationary upper jaw and a lower jaw movable between an open and a closed position, the groove being dimensioned so that one of transfer tubes 20, 25, 26 of the bag sets shown in FIGS. 1, 2 and 3 can be snuggly engaged therein when the lower jaw is in the open position. The elongated body contains a mechanism for moving the lower jaw and it is connected to a radio frequency generator that supplies the energy necessary for sealing and cutting a plastic tube. Pinch valve members 42, 43, 44 are mounted at the periphery of central compartment 35 so that their longitudinal axes are coplanar, and parallel to central axis 31 of the rotor 16, and their heads protrude above the rim of central compartment 35. The position of pinch valve members 42, 43, 44 with respect to separation bag 1 and transfer tubes 20, 25, 26 connected thereto when separation bag 1 is mounted on turntable 37 is shown in dotted lines in FIG. 3. Electric power is supplied to pinch valve members 42, 43, 44 through a slip ring array 45 that is mounted around the lower portion 33 of the rotor shaft.

Support member 36 generally comprises a portion of wall 46 that is tilted with respect to the rotation axis 31 of the rotor 16. A transfer bag secured by an upper portion thereof to an upper part of the tilted wall 46 is pressed against the tilted wall 46 by centrifugation forces during rotation of the rotor 16 and a lower portion of the transfer bag is closer to the axis of rotation than an upper portion thereof. As a result, a liquid contained in the supported transfer bag drains from the supported transfer bag into the separation bag under centrifugation forces.

Turntable 37 comprises a central frustro-conical portion 47, the upper, smaller edge of which is connected to the rim of compartment 35, an annular flat portion 48 connected to the lower, larger edge of the frustro-conical portion 47, and an outer cylindrical flange 49 extending upwards from the outer periphery of the annular portion 48. Turntable 35 further comprises a vaulted circular lid 51 that is secured to flange 49 by a hinge so as to pivot between an open and a closed position. The lid 51 can be blocked in the closed position. When the lid 51 is in the closed position, it defines with the frustro-conical portion 47 and the annular flat portion 48 of the turntable 37 an annular compartment 52 having a radial cross-section that has substantially the shape of a parallelogram. The annular compartment 52 (later the "separation compartment"), which has a fixed volume, is intended for containing the separation bag 1 shown in FIGS. 1 and 2.

Balancing assembly 38, which has generally the shape of a ring, is mounted on the rotor 16 within the space that extends between the upper end of central compartment 35 and the frustro-conical wall 47 of turntable 37. Balancing assembly 38 comprises a ring-shaped housing 53 defining a cavity whose cross-section, along a radial plane, is generally rectangular. The balancing assembly further comprises a plurality of ponderous balls 54 having a diameter that is slightly less than the radial depth of the cavity of housing 53. When the balls 54 are in contact with each other they occupy a sector of housing 53 of about 180 degrees.

The component transferring means comprises a squeezing system for squeezing the separation bag within separation compartment and causing the transfer of separated components into the transfer bags. The squeezing system comprises a flexible annular diaphragm 55 that is so shaped as to line the frusto-conical portion 47 and the annular flat portion 48 of turntable 37, to which it is secured along its smaller and larger circular edges. The squeezing system further comprises a hydraulic pumping station 60 for pumping a hydraulic liquid in and out an expandable hydraulic or squeezing chamber 56 defined between flexible diaphragm 55 and turntable 37, via a duct 57 extending through the rotor 16 from the lower end of lower portion 33 of the rotor shaft to turntable 37. Pumping station 60 comprises a piston pump having a piston 61 movable in a hydraulic cylinder 62 fluidly connected via a rotary fluid coupling 58 to rotor duct 57. Piston 61 is actuated by a stepper motor 63 that moves a lead screw 64 linked to piston rod 61. Stepper motor 63 can be controlled by discrete increments or steps, each step corresponding to a fraction of turn of the axle of motor 63, a small linear displacement of piston 61, and a small determined volume of liquid being pumped in or out of hydraulic chamber 56. Hydraulic cylinder 62 is also connected to a hydraulic liquid reservoir 65 having an access controlled by a valve 66 for selectively allowing the introduction or the withdrawal of hydraulic liquid into and from a hydraulic circuit including hydraulic cylinder 62, rotor duct 57 and the expandable hydraulic chamber 56. A pressure gauge 67 is connected to the hydraulic circuit for measuring the hydraulic pressure therein.

The separation apparatus further comprises sensors 69 for detecting characteristics of the separation process occurring within a separation bag 1 when the apparatus operates. The sensors are embedded in lid at different distances from the rotation axis 31 of the rotor 16. When the lid is closed, the sensors face separation bag 1 to detect an interface gas/liquid, an interface between plasma and a platelet/mononuclear cell layer, or an interface between platelet rich plasma and mononuclear cells, as well as red blood cells. Each sensor can comprise a photocell including an infrared LED and a photodetector.

The separation apparatus further comprises a controller 80 including a control unit (microprocessor) and a memory for providing the microprocessor with information and programmed instructions relative to various separation protocols and to the operation of the apparatus in accordance with such separation protocols. In particular, the microprocessor is programmed for receiving information relative to the centrifugation speed(s) at which the rotor 16 is to be rotated during the various stages of a separation process, and information relative to the various transfer flow rates at which separated components are to be transferred from the separation bag 1 into transfer bags 2, 3, 4. The information relative to the various transfer flow rates can be expressed, for example, as hydraulic liquid flow rates in the hydraulic circuit, or as rotation speeds of stepper motor 63 of hydraulic pumping station 60. The microprocessor is further programmed for receiving, directly or through the memory, information from pressure gauge 67 and from the sensors in the lid and for controlling centrifuge motor 40, stepper motor 63, and pinch valve members 42, 43, 44 so as to cause the separation apparatus to operate along a selected separation protocol. Control unit 80 is also programmed for determining and displaying on a screen 81 of the separation apparatus the actual volume of the components separated during a separation procedure, as well as the actual volume of the composite liquid (for example, whole blood) initially contained in separation bag 1.

The rotor 16 further comprises a central compartment 99, as shown in FIG. 3, for receiving a rotor liner 100 and a bag cradle 101, shown in FIGS. 5 and 6. The bag cradle 101 serves as a bag loading means for loading/unloading at least one satellite bag into/from the central compartment 99 of the rotor 16. The rotor liner 100 guides the bag cradle 101 within the central compartment 99 when the bag cradle 101 is inserted into and removed from the central compartment 99, and for positioning the bag cradle 101 in a determined position within the rotor 16.

The rotor liner 100 comprises a container 120 having a bottom wall 102 and a lateral wall 103, and a flange 104 that is connected to the container 120 slightly below the upper rim of the lateral wall 103. A series of rounded pins 105 arranged on a circle protrude upwards from the flange 104. The size and the location of the pins 105 correspond to the size and location of the holes in the separation bag 1. The pins 105 help position the separation bag 1 on the rotor 16, and prevent the separation bag 1 from moving with respect to the rotor 16 when the rotor 16 is rotating. Along the flat portion of the lateral wall 103 of the rotor liner 100, the flange 104 comprises three aligned cylindrical apertures 106. When the rotor liner 100 is fully inserted in the central compartment 99 of a rotor 16, the pinch valve members 42, 43, 44 extend through the apertures 106 so that the heads of the pinch valve members protrude above the flange 104. Three guiding elements 126, 128, 129 of somewhat complex geometrical shapes partially surround the three apertures 106 and delimit three narrow gates 107 by which tubes engaged in the pinch valve member 42, 43, 44 can be guided into the central compartment 99 along determined directions. The bag cradle 101 further comprises securing means in its upper part, including two lateral recesses 108 opening on its inner surface, for removably receiving and locking the ends of complementary locking elements of a bag holder 101 to be described later. A guide 109, in the form of a narrow tongue, extends from the bottom of each recess 108 towards the lateral edges of the cradle 101 for helping set the bag holder 100 in place.

The cradle 101 performs a loading function, which allows for an easy, lateral arrangement of the bags, transfer tubes and, as the case may be, leukoreduction filter, within the cradle 101, and it allows for an easy, lateral engagement of the pegs 111, 112 of a bag holder 110 into the recesses 108. The bag holder 110 shown in FIG. 8 secures the bags 2, 3, 4 to the cradle 101 in a determined position during the operation of the centrifuge. The bag-holder 110 comprises an elongated flat body 113 in the middle of which a flat U-shaped handling appendage 114 is connected so as to protrude upwards when the bag-holder 110 is mounted in the cradle 101. The elongated flat body 113 has two parallel gutter-like guides 115, 116 on each side. The gutter-like guides 115, 116 are so dimensioned that a tube 20, 22, 25, 26 can be snuggly engaged therein.

The bag-holder 110 further comprises a hanging means in the form of a first couple of pegs 111, 112 connected to the elongated flat body 113 for hanging at least one bag 2, 3, 4 in the cradle 101. The distance between the two pegs 111, 112 is substantially the same as the distance between the holes 14 in bags 2, 3, 4. The cross-section of the pegs 111, 112 substantially fits in the holes 13. The pegs 111, 112 are also used to secure the bag holder 110 to the cradle 101. To this end, the distance between the two pegs 111, 112 is substantially the same as the distance between the two locking recesses 108 in the upper part of the cradle 101. The bag-holder 101 further comprises a second couple of pegs 117, 118 connected to the elongated flat body 101 for releasably securing a bag 2, 3, 4 thereto. Because of the elongated flat body 113 and the first and second couple of pegs 111, 112, 117, 118, the product bags 2, 3, 4 engaged on the pegs occupy a determined position in the central compartment 99 of a rotor 16 when the cradle 101 is assembled to the remaining part of the rotor liner 100.

An example of a first separation protocol aiming at the preparation of four blood components from a whole blood donation, namely a plasma component, a platelet component, a mononuclear cell component and a red blood cell component, is explained below. Alternatively, the protocol can be used for a three-component collection with mononuclear cells being waste or even for at least a two component collection. The operation of the separation apparatus according to the first separation protocol is as follows:

First stage: A bag set as shown in FIG. 1, in which transfer bag 2 contains a volume of whole blood, is set in place in the rotor 16 of a centrifuge (as shown in FIG. 3).

At the onset of the first stage, transfer bag 2 of the bag set of FIG. 1 contains a volume of anti-coagulated whole blood (usually about 500 ml). Collection tube 22 has been sealed and cut close to transfer bag 2. Clamp 24 on transfer tube 27 connecting transfer bag 5 to separation bag 1 is closed. The four transfer bags 2, 3, 4, 5 are superposed one upon another so as to form a stack that is inserted bag loader 36 so that transfer bag 2 is adjacent the tilted wall 46 of bag loader 36. Transfer bags 2, 3, 4, 5 are secured by their upper ears to an upper part of bag loader 36, above the tilted wall 46. In this position, they are substantially located on one side of a plane containing the rotation axis 31 of the rotor 16, and a lower portion of transfer bag 2 containing the volume of whole blood is closer to the rotation axis 31 than an upper portion thereof.

Separation bag 1 is then laid on turntable 37 and pins (not shown) protruding on turntable 37 around the opening of central compartment 35 are engaged in holes 13 of the disk-shaped connecting element 11 of separation bag 1. Transfer tube 20 connecting transfer bag 2 to separation bag 1 is engaged in pinch valve member 42, transfer tube 25 connecting transfer bag 3 to separation bag 1 is engaged in pinch valve member 43, and transfer tube 26 connecting transfer bag 4 to separation bag 1 is engaged in pinch valve member 44. Frangible connector 21 blocking communication between transfer bag 2 and separation bag 1 is broken. Lid 50 of the rotor 16 is closed.

The hematocrit of the blood is unknown or not known precisely. The apparatus is programmed to set a nominal high value for the hematocrit, for example 50%. The actual hematocrit is expected to be less than the nominal value. A predicted sedimentation time, to be used in the fourth stage, below, is computed by the controller 80 according to a process derived from the following formula:

$$Ts = CK(Ds/Rs)Fp/(VsN^2)$$

Wherein
Ts=spin time, sec
Fp=packing factor, dimensionless
N=centrifuge speed, rpm
$K=(30/\pi)^2 g=8.95\times 10^4$ rpm$^2$-cm
C=calibration factor, dimensionless
Ds=characteristic sedimentation distance, cm
Rs=average spin radius of sample volume, cm
Vs=average RBC sedimentation velocity at one g, cm/sec
This equation can be rewritten as follows:

$$Ts = BFvFp$$

Where $$B = CK/(VsN^2)$$

$$Fv = Ds/Rs$$

For a fixed value of N, the centrifugation speed, B is constant. Fv represents the variation in volume between different units of blood. The volume of the blood unit may be measured manually or automatically by the apparatus.

Fp, the packing factor, is dependent on the hematocrit of the blood. It is an object of the present invention to account for variation in this factor by adjusting process parameters during the processing of a unit of blood in order to minimize processing time. Fp is related to hematocrit as follows:

$$Fp = 5Ho/(11(1-H)^2 - Ho/(3(1-H)) - 16Ho^2 + 8Ho + 1.1 \qquad \text{Eq. 1}$$

Where
Ho=starting hematocrit, decimal
H=PRBC (packed red blood cell) hematocrit, decimal Fp is modified during the centrifugation process from the nominal value of Fp (herein after "Fpn") by correcting Ho relative to the initially selected nominal value of Ho (hereinafter "Hon"), as explained below.

Second stage: The anti-coagulated whole blood contained in transfer bag 2 is transferred into the separation bag 1.

At the onset of the second stage, pinch valve member 42 is open and pinch valve members 43, 44 are closed. The rotor 16 is set in motion by centrifuge motor 40 and its rotation speed increases steadily until it reaches a first centrifugation speed (e.g. about 1500 RPM) that is so selected as to be high enough to cause the transfer, under centrifugation forces, of the content of transfer bag 2 into separation bag 1, so that the whole transfer happens in a short period of time; while, at the same time, to be low enough not to cause pressure within transfer bag 2 to substantially exceed a determined pressure threshold above which hemolysis would occur; and to be low enough not to generate shearing forces in the flow of blood entering separation bag 1 that would cause hemolysis. It has been determined that the pressure threshold above which hemolysis occurs in transfer bag 2 is about 10 PSI, and that the maximum rotation speed at which such pressure threshold is not reached and the shearing forces in the blood flow entering the separation bag do not cause hemolysis is about 1800 RPM. At a rotation speed of about 1500 RPM, it takes about one minute for transferring about 500 ml of anti-coagulated blood from transfer bag 2 into separation bag 1. When outer cell 71 detects blood, valve member 43 controlling a flow of fluid through transfer tube 25 connected to transfer bag 3 (in which a plasma component will be later transferred) is opened for a predetermined amount of time (for example, about 30 seconds) so as to allow air to vent from separation bag 1 when blood pours therein. If outer cell 71 has not detected blood within a predetermined period of time following the start of the centrifugation process, control unit 80 causes the rotor 16 to stop and an alarm to be emitted. This could happen in particular if frangible connector 21 has inadvertently not been broken.

Third stage: The air present in separation bag 1 is purged into transfer bag 2, in which the mononuclear cell component is to be later transferred.

At the onset of the third stage, the whole content of transfer bag 2 has been transferred into separation bag 1, pinch valve member 42 is open, and pinch valve members 43, 44 are closed. The rotor 16 rotates at the first rotation speed (about 1500 RPM). Pumping station 60 is actuated so as to pump hydraulic liquid at a constant flow rate (for example, about 240 ml/min) into hydraulic chamber 56 and consequently squeeze separation bag 1. The air present in separation bag 1 is expelled into transfer bag 2 for the mononuclear cell component. After a predetermined period of time following the detection of an interface air/liquid by sensor 70, the pumping station 60 is stopped and pinch valve member 42 is closed. A small residual volume of air remains in separation bag 1.

Fourth stage: The blood within the separation chamber is sedimented to a desired level.

At the onset of this stage, pinch valve members 42 and 43 are closed. The speed of the rotor 16 is increased steadily until it reaches a second, high, centrifugation speed (for example, about 3200 RPM, so-called "hard spin") at which the blood components will sediment at the desired level. Pinch valve member 44 is open so that any additional air can be expelled to platelet bag 4. To expel the air the pumping station is activated to pump hydraulic fluid at a constant flow rate to the hydraulic chamber to squeeze the separation bag 1. Squeezing continues until the hydraulic pressure is a predetermined variation from the constant pressure as described below.

In the prior art, the rotor 16 has been rotated at the second centrifugation speed for a predetermined period of time or "sedimentation time" (for example, about 220 seconds), which is selected so that, whatever the hematocrit of the whole blood initially transferred in the separation chamber 1, the blood sediments therein at the end of the predetermined period to a point where the hematocrit of the outer annular red blood cell layer is about 90 and the inner annular plasma layer is substantially devoid of cells. In the present method, in contrast, the rotor begins rotation at the second rotational speed. The blood begins to sediment into different layers. The RBC interface will begin to form and will move radially outwardly away from the center of rotation. The sensor 69 detects the passage of the RBC interface. Preferably, the sensor is located where it is expected that the red blood cells will have been packed to a hematocrit of 85%. Packing the red blood cells to 85% hematocrit usually takes about one half of the sedimentation time. If the RBC interface is detected earlier than one half of a predicted sedimentation time, the sedimentation time can be shortened.

Fp is modified during the centrifugation process from the nominal value of Fp (herein after "Fpn" by correcting Ho relative to the initially selected nominal value of Ho (hereinafter "Hon"). Therefore, the initial estimate of the spin time, or nominal spin time (hereinafter "Tsn") may be expressed as $$Tsn = BFvnFpn$$

A more accurate value for the volume of the blood unit may be obtained by manual measurement (e.g., weighing with calculation of volume) or by automatic measurement by the centrifuge apparatus. A more accurate value for the packing factor Fp will be obtained from the elapsed time Td from the beginning of centrifugation to the arrival of the red blood cell interface at the optical sensor, as will be explained below. The corrected spin time will be given by the following corrected spin time equation:

$$Ts = (Fv/Fvn)(Fp/Fpn)Tsn \qquad \text{Eq. 2}$$

Fpn is corrected to actual Fp by correcting Hon to Ho, based on the elapsed time Td. As noted above, spin time is dependant not only on hematocrit, but also on sedimentation velocity Vs. However, because Vs cannot be directly determined, it is treated as a fixed value, part of the value B. Variation in Vs is included in the correction for Ho because the elapsed time Td is dependent on both the hematocrit and the sedimentation velocity.

The RBC interface detector or photo sensor 69 is located at a radius Rd from the center of rotation of the centrifuge. Under nominal conditions, including a selected centrifuge speed, the expected or nominal arrival time Tdn of the RBC interface at the sensor 69 is $$Tdn = B(Fvn)(Fpdn)$$

Where Fpdn is the expected or nominal packing factor at the photo sensor located at radius Rd, which will, of course, be less than the final packing factor, that is, the initial hematocrit of the blood unit is less than the hematocrit when the RBC interface reaches the photo sensor 69 which is less than the final hematocrit at the end of the separation process. With a measured volume and a measured time Td for the arrival of the RBC interface, the apparatus can calculate a corrected value of the initial hematocrit Ho as follows:

$$Ho = Hon + [(Fvn/Fv)(Td/Tdn) - 1]Fpdn/[(Fpd - Fpdn)/(Ho - Hon)] \quad \text{Eq. 3}$$

The corrected value for the hematocrit may then be used in Eq. 1 to obtain the corrected packing factor Fp. The corrected spin time Ts is calculated using Eq. 2.

It is preferred that the radial position of the photo sensor 69 be chosen such that the value of [(Fpd−Fpdn)/(Ho−Hon)] is greater than zero (see Eq. 3, above) and large enough to give good discrimination for Ho. Preferably Rd should be selected such that the hematocrit when the RBC interface reaches the photo sensor would be expected to be about 80 or greater. Secondly, Rd should be chosen such that Td is approximately Ts/2. This implies that enough packing will have been done when the RBC interface reaches the sensor for an accurate calculation of Ho, but that sufficient process time would be remaining to allow ample time for correction. For example, if an Hdn of 80 were selected, and if Ho was actually between 30 and 50, Fpn would be between 5 and 6 and [(Fpd−Fpdn)/(Ho−Hon)] would be greater than 1. Td would be expected to be between 60% and 65% of Ts for a final product hematocrit of 85 and between 30% and 35% for a final product hematocrit of 90.

In more detail, at the outcome of this sedimentation stage, the separation bag 1 exhibits four layers: a first inner layer mainly comprising plasma, a second intermediate layer mainly comprising platelets, a third intermediate layer mainly comprising white blood cells (lymphocytes, monocytes and granulocytes), and a fourth outer layer mainly comprising red blood cells, wherein the third and fourth layers partially overlap (the granulocytes are in part embedded in the fourth layer).

Fifth stage: A plasma component is transferred into transfer bag 3.

At the onset of this stage, the pinch valve member 42 and 43 are closed. Pinch valve member 44 remains open. The rotor 16 continues to rotate at the same high centrifugation speed as in the sedimentation stage. After a predetermined period of time after sensor 72 has detected the outward moving plasma/blood cell interface, which can happen before the end of the predetermined sedimentation period, pinch valve member 43 controlling access to transfer bag 3 is opened. Pumping station 60 is actuated so as to pump hydraulic liquid at a constant flow rate (for example, about 150-220 ml/min) into hydraulic chamber 56. The expanding hydraulic chamber 56 squeezes separation bag 1 and causes the transfer of plasma into transfer bag 3 and some plasma into transfer tube 26. Pinch valve 44 is closed at the turning point of increasing pressure to constant pressure as described below. Thus the majority of the plasma is transferred to bag 3. The pinch valve member 43 is closed after a predetermined period of time has elapsed following the detection of the inward moving plasma and platelet (or mononuclear cell) interface by the intermediate sensor 70. At the end of this stage, a first, larger, fraction of the total volume of plasma is in transfer bag 3, a second, smaller, fraction of the total volume of plasma remains in separation bag 1, and a third small fraction of the total volume of plasma has entered transfer tube 26. The transfer flow rate of the plasma component (which is directly related to the flow rate of the hydraulic fluid or liquid) is selected to be as high as possible without disturbing the platelet layer so as to avoid contaminating the plasma component with platelets.

Control unit 80 determines the volume of plasma that has been transferred into transfer bag 3 in the following manner: first, it determines when plasma actually starts pouring into transfer bag 3; second, it counts the number of steps performed by stepper motor 63 between the time plasma actually starts pouring into transfer bag 3, and the time pumping station 60 stops pumping hydraulic liquid into hydraulic chamber 56 after sensor 70 has detected an interface between plasma and the platelet/mononuclear cells; finally, the control unit 80 calculates, from the counted number of steps and the determined small volume associated to one step, the total volume of hydraulic liquid pumped into hydraulic chamber 56 during this stage, which corresponds to the volume of plasma in transfer bag 3.

Control unit 80 determines when plasma actually starts pouring into transfer bag 3, in the following manner: it continuously records discrete successive values of the pressure of the hydraulic liquid as measured by pressure sensor 67, and it simultaneously analyses how the pressure evolves, for example by calculating, each time a new pressure value is recorded, from the average of the last four measured values, the slope of a curve representing the evolution of the pressure with respect to time, and by comparing the series of slopes so calculated; control unit 80 determines the point in time at which plasma start pouring into transfer bag 3 as corresponding to a drastic turning point between a first phase of steadily increasing pressure and a second phase of substantially constant pressure. This constant pressure as determined by pressure gauge 37 is recorded in the controller as pressure P. This turning point is also the signal for the control unit 80 to close valve 44. Control unit 80 can be programmed to display the actual volume of plasma in transfer bag 3 on screen 81.

Control unit 80 also determines the volume of anti-coagulated whole blood that has been transferred into separation bag 1 during the second stage, in the following manner: it first counts the number of steps performed by stepper motor 63 between the time pumping station 60 starts pumping hydraulic fluid into hydraulic chamber 56 at the third stage (transfer of air into transfer bag 2), and the time when plasma actually starts pouring into transfer bag 3, as determined above; second, control unit 80 calculates, from the counted number of steps and the determined small volume associated to one step, the total volume of hydraulic liquid pumped into hydraulic chamber 56 until separation compartment 52 does not contain air anymore; finally, control unit 80 calculates the volume of anti-coagulated blood that is in separation chamber 1, by subtracting the volume of hydraulic liquid so calculated from a fixed volume, stored in the memory of control unit 80. This fixed volume corresponds to the fixed volume of separation compartment 52, minus the volume of diaphragm 55, minus the volume of the two superposed rings of plastic sheet delimiting separation chamber 6, and minus a fixed residual volume of hydraulic liquid in hydraulic chamber 56. Control unit 80 can display the actual volume of anti-coagulated blood in separation bag 1 on screen 81.

Sixth stage: The platelet component is transferred into transfer bag 4.

Pinch valve member 44 controlling the access to transfer bag 4 is open and pinch valve member 42, 43 remain closed. The rotor 16 continues to rotate at 3200 rpm. Pumping station 60 is actuated so as to pump hydraulic liquid at a first platelet flow rate into hydraulic chamber 56 and consequently squeeze separation bag 1 and cause the transfer of the platelet component and the smaller fraction of the plasma component in tube 26 into transfer bag 4. The first platelet flow rate for the platelets (for example, about 15 ml/min) is substantially lower than the flow rate (for example, about 150-220 ml/min) at which the plasma component is transferred into transfer bag 3 in the fifth stage. The first transfer flow rate of the platelet component (which is directly related to the first flow rate of the hydraulic fluid) is selected to be high enough for preventing the suspended platelets from sedimenting, without, at the same time, triggering the activation of the platelets. After a predetermined volume of platelets has been collected as described below and after sensor 73 detects an interface between the suspended platelets and mononuclear/red blood cells, the pumping station is stopped and pinch valve member 44 is then closed.

Control unit 80 determines the volume of the platelet component that has been transferred into transfer bag 4 at this point in the procedure in the following manner: it first counts the number of steps performed by stepper motor 63 between the time pumping station 60 starts pumping hydraulic fluid into hydraulic chamber 56 following the opening of pinch valve member 44, and the time pumping station 60 is stopped after sensor 73 has detected the interface between the suspended platelets and the mononuclear/red blood cells; second, control unit 80 calculates, from the counted number of steps and the determined small volume associated to one step, the total volume of hydraulic liquid pumped into hydraulic chamber 56 during this stage, which corresponds to the volume of the platelet component transferred to transfer bag 4. This volume is stored in the control unit 80 memory.

Seventh stage: The flow of hydraulic fluid is reversed.

After the closure of pinch valve member 44 the rotor 16 is slowed to approximately 900 rpm. The hydraulic system is reversed to withdraw a volume Vx of hydraulic fluid from hydraulic or squeezing chamber 56 releasing some of the squeezing pressure on separation bag 1. During this reversal of hydraulic fluid separation is maintained between any platelets and the red blood cells and mononuclear layers in separation bag 1. Vx is selected by the controller based on final desired platelet volume as will be more fully explained with respect to the expression or spurt of platelets below. Vx can be indicative of the final plasma concentration in the final platelet product. Variations of Vx can be used to vary the plasma content and to provide plasma rich platelets.

Eighth stage: Plasma component is returned to separation bag 1 (remixing).

The reverse pumping of hydraulic pumping station 60 is stopped, the rotor speed is increased to 3200, and pinch valve 43 is opened. This withdraws a volume of plasma Vx from transfer bag 3 corresponding to the removed volume of hydraulic fluid Vx as the transfer amount of the plasma is directly related to the transfer amount of the hydraulic fluid removed from hydraulic chamber 56. The returned plasma remixes with the platelets and red blood cells to assure any residual platelets are separated from the red blood cells. At this hard spin the red blood cells sediment out rapidly into a red blood cell layer.

Ninth stage: The hydraulic fluid in the hydraulic chamber 56 is increased to increase the pressure on separation bag 1 with all valves closed.

All the valves 42, 43, and 44 are closed. The rotor 16 continues to rotate at a hard spin or approximately 3200 rpm. Hydraulic pumping station 60 is activated to return hydraulic fluid to hydraulic or squeezing chamber 56. Hydraulic chamber 56 receives hydraulic fluid until the pressure exerted on separation bag 1 is pressure P plus ΔP. That is, the pressure is raised higher than the constant pressure for expression to assure that the separation bag 1 is at a pressure for rapid expression or spurting as will be more fully explained below.

Tenth stage: The platelet line is cleared.

After hydraulic chamber 56 is filled with hydraulic fluid as set forth in the ninth stage above, pinch valve member 44 is opened while pinch valves 42 and 43 remain closed. The rotor 16 continues to rotate at 3200 rpm. Some residual platelets and plasma from separation bag 1 are rapidly expressed or caused to spurt to transfer tube 26 connected to transfer bag 3 by the over pressure applied by hydraulic chamber 56. Hydraulic pumping station 60 is stationary during this rapid expression or spurt period as all the expression is the consequence of the built up pressure from the hydraulic fluid already present in hydraulic chamber 56. This spurt expression clears the transfer line 26 of any residual platelets contained therein from the platelet expression of the sixth stage.

Control unit 80 determines the volume of the spurted platelet and plasma component that is transferred into transfer bag 4 at this point in the procedure in the following manner: it first counts the number of steps performed by stepper motor 63 between the time pumping station 60 starts pumping hydraulic fluid into hydraulic chamber 56 until the pressure on the separation bag 1 is P and ΔP and the pinch valve member 44 is opened. The control unit 80 calculates, from the counted number of steps and the determined small volume associated to one step, the total volume of hydraulic liquid pumped into hydraulic chamber 56 during this stage, which corresponds to the volume of the platelet with any plasma component rapidly expressed or transferred to transfer bag 4 during this stage. This volume is stored in the control unit 80 memory.

Eleventh stage: Remaining platelets are collected

Pinch valve 44 remains open. Hydraulic pumping station 60 provides a low flow rate of the remaining platelets/plasma or plasma rich platelets of approximately 15 ml/min until a predetermined time after the top of the red blood cell layer is detected by inner photocell 73. The predetermined time assures that the maximum number of platelets will be collected. The centrifuge or rotor 16 continues to rotate at 3200 rpm. After the predetermined time, pinch valve 44 is closed and platelet collection is completed.

Control unit 80 determines the volume of the platelet component that has been transferred into transfer bag 4 during this stage in the following manner: it first counts the number of steps performed by stepper motor 63 between the time pumping station 60 is ramped up to start pumping hydraulic fluid into hydraulic chamber 56 and the time pumping station 60 is stopped after sensor 73 has detected the interface between the suspended platelets and the mononuclear/red blood cells; second, control unit 80 calculates, from the counted number of steps and the determined small volume associated to one step, the total volume of hydraulic liquid pumped into hydraulic chamber 56 during this stage, which corresponds to the volume of the platelet component transferred to transfer bag 4 during this stage. To determine the total platelet volume, the control unit 80 retrieves and adds the determined volumes from the platelet collections in the sixth, tenth and eleventh stages. The control unit 80 can be programmed to display this total volume on the display screen 81.

Twelfth stage: A mononuclear cell component is transferred into transfer bag 2.

The twelfth stage can start as soon as pinch valve member 44 is closed at the end of the eleventh stage. At the onset of this twelfth stage, the three pinch valve members 42, 43, 44 are closed. The rotor 16 is rotated at the same centrifugation speed as previously with the flow rate being adjusted by hydraulic pumping station 60. Pinch valve member 42 controlling the access to transfer bag 2 is opened and hydraulic pumping system 60 is actuated so as to pump hydraulic liquid at a constant flow rate (for example, about 60 ml/min) into hydraulic chamber 56. The expanding hydraulic chamber 56 squeezes separation bag 1 and causes the transfer, into first transfer bag 2, of a mononuclear cell component comprising lymphocytes, monocytes, and a small amount of red blood cells. Pumping system 60 is stopped and pinch valve member 42 is closed after a predetermined volume (e.g., between 10 and 20 ml) has been transferred into transfer bag 2. The rotor 16 continues to rotate at 3200 rpm to maintain separation between the red blood cell and mononuclear cell layers.

Control unit 80 determines the actual volume of the mononuclear cell component in transfer bag 2 by adding the volume of the mononuclear cell component actually transferred into transfer bag 2, which volume corresponds to the number of steps performed by the stepper motor between the opening and the closing of pinch valve member 42, to an empirically determined volume of whole blood remaining in transfer bag 2, which is stored in the memory of the control unit. Control unit 80 can display the actual volume of the mononuclear cell component in transfer bag 2 on screen 81.

Thirteenth stage: The centrifugation process is ended.

The rotation speed of the rotor 16 is decreased until the rotor 16 stops, pumping system 60 is actuated and reversed so as to pump the hydraulic liquid from hydraulic chamber 56 at a high flow rate (for example, about 800 ml/min) until hydraulic chamber 56 is substantially empty, and pinch valve members 42, 43, 44 are actuated so as to seal and cut transfer tubes 20, 25, 26. Red blood cells remain in separation bag 1.

Fourteenth stage: A red blood cell component is transferred into transfer bag 5.

Control unit 80 determines the volume of red blood cells remaining in separation bag 1 by subtracting, from the previously determined volume of anti-coagulated whole blood the previously determined volumes of plasma component, platelet component and mononuclear cell component. Lid 50 of the rotor 16 is opened and separation bag 1 connected to transfer bag 5 is removed therefrom. Clamp 24 on transfer tube 27 is opened. Frangible connector 29 blocking communication between transfer bag 5 and leukoreduction filter 28 is broken. The storage solution contained in transfer bag 5 is allowed to flow by gravity through filter 28 and into separation bag 1 where it is mixed with the red blood cells so as to lower the viscosity thereof. The content of separation bag 1 is then allowed to flow by gravity drain through filter 28 and into transfer bag 5. The white blood cells (granulocytes and residual monocytes and lymphocytes) are trapped by filter 28, so that the ultimate packed red blood cell component in the bag 5 is substantially devoid from white blood cells.

Control unit 80 can also determine the volume of red blood cells in transfer bag 5, which will result from the actual subsequent transfer of red blood cells from separation bag 1 into transfer bag 5 at the outcome of the fourteenth stage of the first separation protocol. Control unit 80 calculates the volume of red blood cells by subtracting, from the previously determined volume of anti-coagulated whole blood, the previously determined volumes of plasma component, platelet component, mononuclear cell component, and the internal volume of leukoreduction filter 28, and adding to the result the known volume of red blood cell storage solution contained in transfer bag 5. Control unit 80 can be programmed to cause either one of the actual volume of the red blood cell component in separation bag 1 and the actual volume of the red blood cell component in transfer bag 5, or both, once determined, to be displayed on screen 81.

Although the over-pressure expression has been described particularly with respect to the collection of platelets it is understood that similar expression systems can be used for other blood components. Although the instant invention has been described with respect to the movement of the plasma component from the transfer bag to the separation vessel it is understood that similar principles can be used to collect other components when it is desirable to collect a component in two stages for maximum collection amount or desirable to mix components. The above protocol has been described with respect to a four component collection, namely a first component plasma, a second component platelets, a third component mononuclear cells and a fourth component red blood cells. It is understood, however, that the concepts can be used for at least a two-component collection or a three-component collection. It is also further understood that use of numbers, such as the designation of first and second, etc. are only for explanation purposes and the numbers do not necessarily imply any particular order.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. A method of separating blood into at least a first component and a second component, comprising
providing a centrifuge blood separation apparatus with a quantity of whole blood;
calculating a predicted processing time for said quantity of whole blood;
centrifuging a separation bag containing said whole blood so as to cause the sedimentation of at least a first component and a second component;
transferring some of the first component to a first transfer bag;
detecting time of passage of a red blood cell interface at a pre-selected location in the separation bag;
adjusting said predicted processing time based on the time of passage of the red blood cell interface.

2. The method of claim 1 further comprising the steps of
selecting a nominal hematocrit value for said whole blood such that an actual hematocrit value is expected to be less than said nominal hematocrit; and
calculating said predicted processing time, at least in part, from said nominal hematocrit value.

3. The method of claim 2 further comprising calculating a packing factor from said nominal hematocrit value.

4. The method of claim 3 wherein said packing factor, Fp, is calculated as:

$$Fp = 5Ho/(11(1-H)^2) - Ho/(3(1-H)) - 16Ho^2 + 8Ho + 1.1$$

Where
Ho is equal to a starting hematocrit; and
H is equal to a packed red blood cell hematocrit.

5. The method of claim 4 wherein said packing factor is modified during a centrifugation process from an initial nominal value to a calculated value based on a determination of a donor's hematocrit.

6. The method of claim 5 wherein said red blood cell interface is detected by a photo sensor.

7. The method of claim 6 wherein the photo sensor is located in a separation chamber for receiving said separation bag and is placed at a location such that the hematocrit when the red blood cell interface reaches the photo sensor would be expected to be 80 or greater.

8. The method of claim 7 wherein an expected time for said red blood cell interface to reach said photo sensor after a beginning of centrifugation is about one half an expected total sedimentation time.

9. The method of claim 1 wherein calculating said predicted processing time comprises calculating said predicted processing time in part from a predicted sedimentation time.

10. The method of claim 9 wherein said predicted sedimentation time, Ts, is computed by said controller according to the following formula:

$$Ts = CK(Ds/Rs)Fp/(VsN^2)$$

Wherein
Ts is spin time,
Fp is a packing factor,
N is centrifuge speed,
K is $(30/\pi)^2 g$, which is $8.95 \times 10^4$ rpm$^2$-cm
C is a calibration factor,
Ds is a characteristic sedimentation distance,
Rs is an average spin radius of sample volume, and
Vs is an average RBC sedimentation velocity at one g.

* * * * *